United States Patent
Van Der Puy et al.

(10) Patent No.: US 7,902,410 B2
(45) Date of Patent: Mar. 8, 2011

(54) PROCESS FOR THE MANUFACTURE OF FLUORINATED ALKANES

(75) Inventors: Michael Van Der Puy, Amherst, NY (US); George R. Cook, Buffalo, NY (US); Peter H. Scheidle, Wheatfield, NY (US); Kevin D. Uhrich, Alden, NY (US)

(73) Assignee: Honeywell International Inc., Morristown, NJ (US)

( * ) Notice: Subject to any disclaimer, the term of this patent is extended or adjusted under 35 U.S.C. 154(b) by 782 days.

(21) Appl. No.: 11/588,671

(22) Filed: Oct. 27, 2006

(65) Prior Publication Data

US 2007/0123741 A1    May 31, 2007

Related U.S. Application Data

(60) Provisional application No. 60/733,355, filed on Nov. 3, 2005.

(51) Int. Cl.
   C07C 17/00    (2006.01)
   C07C 21/00    (2006.01)
(52) U.S. Cl. ........................................ 570/175
(58) Field of Classification Search .............. None
   See application file for complete search history.

(56) References Cited

U.S. PATENT DOCUMENTS

| | | | |
|---|---|---|---|
| 5,672,787 A | | 9/1997 | Bielefeldt et al. |
| 5,672,803 A | | 9/1997 | Smith et al. |
| 5,679,875 A | | 10/1997 | Aoyama et al. |
| 5,714,655 A | * | 2/1998 | Yamamoto et al. ........... 570/176 |
| 6,734,332 B1 | | 5/2004 | Slaugh et al. |
| 7,230,146 B2 | | 6/2007 | Merkel et al. |
| 2004/0119047 A1 | | 6/2004 | Singh et al. |

FOREIGN PATENT DOCUMENTS

| | | |
|---|---|---|
| CA | 2152031 | 12/1995 |
| EP | 0442087 | 8/1991 |
| EP | 0644173 | 3/1995 |
| EP | 0688751 | 12/1995 |
| EP | 0726243 | 8/1996 |
| JP | 08165256 | 6/1996 |

OTHER PUBLICATIONS

Meriam-Webster online dictionary [online], retreived on Aug. 26, 2009. Retreived from the internet at <URL: http://www.merriam-webster.com/dictionary/stage>.*
Knunyants Il, et al "Reactions of Fluoro Olefins Communication 13. Catalytic Hydrogenation of Perfluoro Olefins", 1960, Bulletin of the Academy of Sciences of the USSR, Division of Chemical Sciences, pp. 1312-1317, XP000578879, ISSN: 0568-5230.
Kiyoshi Endo et al., "Monomer-Isomerization Polymerization-XXVI. The Case of 2-Butene in the Presence of Isobutene with Ziegler-Natta Catalyst," Eur. Polym. J., vol. 28, No. 2, pp. 153-157 (1992).

* cited by examiner

*Primary Examiner* — Daniel M Sullivan
*Assistant Examiner* — Clinton Brooks
(74) *Attorney, Agent, or Firm* — Bruce Bradford

(57) ABSTRACT

A process for the production of fluorinated alkanes by contacting a feed stream containing a fluorinated olefin and a reducing agent, preferably with a first amount of catalyst to produce a fluorinated alkane, at a first conversion level, wherein a first effluent stream contains unreacted fluorinated olefin and reducing agent; and contacting the first effluent stream under conditions effective to produce a higher level of conversion than said conversion level.

15 Claims, 1 Drawing Sheet

PROCESS FOR THE MANUFACTURE OF FLUORINATED ALKANES

CROSS-REFERENCES TO RELATED APPLICATIONS

This application is related to and claims the priority benefit of provisional application Ser. No. 60/733,355, filed on Nov. 3, 2005, which is incorporated herein by reference.

Also incorporated herein by reference are of the following U.S. Applications which are filed concurrently herewith and identified by U.S. Ser. Nos. 11/588,465; 11/588,466; and 11/588,464.

BACKGROUND OF THE INVENTION

Fluorinated alkanes, as a class, have many and varied uses, including as chemical intermediates, blowing agents and refrigerants.

Several methods for preparing fluorinated alkanes, particularly hydrofluorocarbons (HFCS) are known. For example, Chem Abstract 55:349c (I. L. Knunyants, M. P. Krasuskaya, and E. I. Mysov, Izvest. Akad. Nauk S. S. S. R., Otdel. Khim. Nauk. 19060, 1412), describe the reduction of a fluorinated olefin, particularly CF3CF=CFH over palladium catalyst (Pd—Al2O3) at room temperature to give a selectivity to the saturated analog ($CF_3CHFCFH_2$) of about 60% and a selectivity to $CF_3CFHCH_3$ of about 30%. Chem. Abstract 125: 167319 (JP 08165256 A2) discloses the reduction of $CF_3CF=CF_2$ with hydrogen in a liquid phase reaction using palladium catalysts supported by $BaSO_4$ and/or activated carbon.

Applicants have discovered that the processes of the type described above have disadvantages and/or are not as effective and/or economical as would be practically necessary for large scale commercial production. For example, applicants have come to appreciate that it is generally difficult, costly or not possible, by following the teachings of the above publications alone, to achieve a process having at once a high degree of ultimate conversion and a high degree of selectivity to the desired fluorinated alkane. Applicants have also come to appreciate that none of the above publications disclose even the problem of processes that are burdened with either a low selectivity to the desired fluorinated alkane and/or a throughput capacity that is economically not acceptable on a commercial scale. In other words, the prior processes in general tend to teach that higher selectivity in such processes can come only at the cost of low throughput rates. While such processes may be acceptable for non-commercial operations, applicants have come to appreciate that such processes are disadvantageous for use in commercial production and have proceeded counter to conventional teaching to develop processes which are capable of achieving at once high throughput rates and high selectivity.

SUMMARY OF THE INVENTION

Applicants have discovered, in one aspect of the present invention, processes for the synthesis of fluorinated alkanes, and preferable fluorinated alkanes having from three to six carbon atoms and preferably a degree of fluorine substitution of from about 3 to about 5.

Preferred processes of the present invention comprise reacting a fluorinated olefin starting material having substantially the same number of carbon atoms as the desired fluorinated alkane and the same degree of fluorine substitution. Preferably the fluorinated olefin starting material is exposed to reaction conditions effective to produce a reaction product containing one or more fluorinated alkanes having the same number of carbons atoms as the olefin. In one preferred aspect of the present invention, this olefin conversion step comprises a reaction that is sometimes referred to herein for convenience, but not necessarily by way of limitation, has a multistage reduction or hydrogenation step.

According to one aspect of the present invention, therefore, the present processes preferably comprise the steps of:
(a) hydrogenating in a multistage reaction an olefinic compound of formula (I)

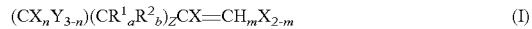

under conditions effective to form at least one fluorinated alkane of formula (II)

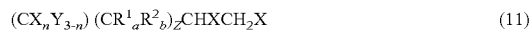

where:
each X is independently Cl, F, I or Br;
each Y is independently H, Cl, F, I or Br;
each $R^1$ is independently H, Cl, F, I, Br or unsubstituted or halogen substituted methyl or ethyl radical;
each $R^2$ is independently H, Cl, F, I, Br or unsubstituted or halogen substituted methyl or ethyl radical;
n is 1, 2 or 3;
a and b are each 1 or 2, provided that a+b=2;
m is 0, 1 or 2; and
Z is 0, 1, 2 or 3.

In certain preferred embodiments, the reactant of formula (I) comprises a three carbon olefin of formula (IA) wherein z is 0, namely

to produce a three carbon alkane of formula (IIA) as follows:

where X, Y, n, and m are all as indicated above.

In certain highly preferred aspects of such embodiments, a saturated terminal carbon of the compounds of formulas (I) or (IA) is fully substituted with fluorine (for example, n on the saturated terminal carbon is 3 and each X on that carbon is F), and even more preferably n is 3 and each X in the compound is F.

For three carbon embodiments of such preferred aspects, the compound of Formula (IA) is preferably a fluoropropene having from three to six fluorine substituents, and potentially other halogen substituents, including for example hexafluoropropene (that is, Z is 0, n is 3, m is 0, and all X are F) or pentafluoropropene (that is, Z is 0, n=3, m is 1, and all X are F), and the compound of formula (IIA) preferably comprises, and more preferably is selected from the group consisting of, one or more of the following fluorinated alkanes: chlorotrifluoropropane (HCFC-244) and pentafluoropropane (HFC-245), and hexafluoropropane (HFC-236), including all isomers of each of these, but preferably 1-chloro, 1,3,3,3-tetrafluoropropane (HCFC-244fa), 1,1,1,3,3-pentafluoropropane (HFC-245fa), 1,1,1,2,3-pentafluoropropane (HFC-245eb), and 1,1,1,2,3,3-hexafluoropropane (HFC-236ea).

In preferred embodiments, the converting step (a) wherein the olefin is converted to an alkane is carried out under conditions effective to provide a formula (I) conversion of at least about 40%, more preferably at least about 55%, and even more preferably at least about 70%. In certain preferred embodiments the conversion is at least about 90%, and more preferably about 99%. Further in certain preferred embodiments, the conversion of the compound of formula (I) to produce a compound of formula (II) is conducted under conditions effective to provide a formula (II) selectivity of at least about 60%, more preferably at least about 80%, and more preferably at least about 90%, and even more preferably about 100%.

DETAILED DESCRIPTION

Figure 1:
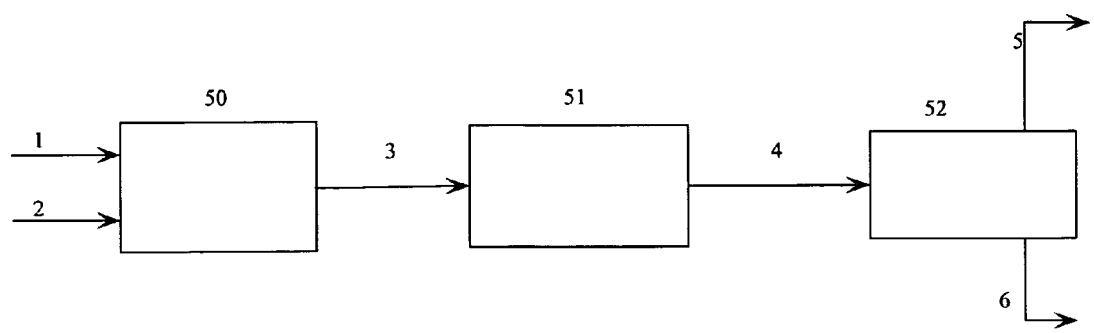
FIG. 1 is a block flow diagram showing a process of which the present multi-stage conversion process is a part.

One embodiment of the present invention will now be described in connection with FIG. 1 in which a feed stream 1 comprising at least one fluorinated olefin having a degree of fluorine substitution of N is subjected to a first converting step 50 in accordance with the process of the present invention. The converting step 50 preferably involves also a feed stream 2 comprising a reducing agent. The converting step 50 preferably includes providing one or more reaction vessels, at least one of which preferably contains a reduction or hydrogenation catalyst, and introducing streams 1 and 2 into the vessel(s) under conditions effective to achieve the desired conversion in a multi-stage reaction operation as described herein.

Although the streams 1 and 2 in the figure are shown for convenience as being separate streams, this is done for convenience and the present invention is not so limited. For example, the streams could in certain embodiments be combined outside the vessel and then introduced to the vessel together, or in other embodiments stream 1 and stream 2 might each comprise several separate streams, each of which is introduced into the vessel(s) at different times and/or at different locations. This same convention has been used and applies herein throughout to all use of the term "stream," both in the text and in the figures, unless specifically indicated otherwise.

The preferred converting step 50 produces at least one reaction product stream 3 which contains a fluorinated alkane in accordance with the present invention. Some or all of stream 3 may be used, for example, as a reactant in conversion step 51 wherein the fluorinated alkane in stream 3 is converted to a fluorinated olefin have a degree of fluorine substitution of N−1, followed by a separation step 52 in accordance with an invention described more fully in copending application bearing Ser. No. 11/588,464.

Although it is contemplated that the reduction step of the present invention may be conducted in batch operation, it is preferred that the reduction reaction is carried out as a substantially continuous operation. Furthermore, while is possible that the reduction reaction may involve in certain embodiments a liquid phase reaction, it is contemplated that in preferred embodiments the reduction reaction comprises, and even more preferably consists of, at least two vapor phase reaction stages.

With respect to the number of reaction stages, applicants have found surprisingly and unexpectedly that overall reaction conversion and selectivity can be achieved at relatively high levels, and/or at relatively high throughput rates, by the use of at least two reaction stages wherein the first stage of reaction is conducted under conditions effective to achieve a first, relatively low rate of conversion to produce a first stage reaction effluent, and at least a second stage of reaction which is fed by at least a portion of said first stage effluent and which is conducted under conditions effective to achieve a second rate of conversion higher than said first rate. Preferably, reaction conditions are controlled in each of the first and second stages in order to achieve the desired conversion in accordance with the present invention. As used herein, the term "reaction conditions" is intended to include the singular and means control of any one or more processing parameters which can be modified by the operator of the reaction to produce the conversion of the feed material in accordance with the teachings contained herein. By way of example, but not by way of limitation, conversion of the feed material may be controlled or regulated by controlling or regulating any one or more of the following: the temperature of the reaction, the flow rate of the reactants, the presence of diluent, the amount of catalyst present in the reaction vessel, the shape and size of the reaction vessel, the pressure of the reaction, and any one combinations of these and other process parameters which will be available and known to those skilled in the art in view of the disclosure contained herein.

Applicants have found that in preferred embodiments the step of controlling the conversion in the first stage of the hydrogenation reaction is achieved by judicious selection and control of the amount of catalyst present in the first stage of reaction relative to the feed rate of one or more of the reactants and/or by judicious selection and control of the reaction temperature, and preferably by judicious selection and control of both of these process parameters. The step of selecting the amount of catalyst to be used in the first stage of reaction preferably includes the step of estimating the amount of catalyst theoretically needed to convert 100% of the feed material. Such an estimate can be obtained by any and all known methods for making such an estimate, which should be apparent to those skilled in the art in view of the teachings contained herein. In addition, the step of selecting the amount of catalyst may also involve conducting bench, pilot or similar studies to determine the amount of the particular catalyst being used which is needed to convert 100% of the feed material under the feed rate and other process parameters which have otherwise been chosen. Based upon this estimate, the preferred embodiments of the present invention then include the step of providing in the first stage of reaction an amount of catalyst that is substantially below the amount required for 100% conversion, and even more preferably is sufficiently low so as to result in a conversion of the feed olefin of from about 10% to about 60%, more preferably from about 10% to about 40%, and even more preferably from about 10% to 25%. Once again, those skilled in the art will appreciate that the step of selecting the amount of catalyst may further include running additional bench, pilot or other studies with the reduced amount of catalyst and adjusting the amount of catalyst accordingly. It is contemplated that all such studies and estimates can be achieved without undue experimentation in view of the teachings contained herein.

In preferred embodiments, therefore, the step of controlling conversion in the first reactor stage comprises feeding the olefin reactant into the first stage of reaction at a rate that is substantially above, and at least 60% about 90% above the productivity of the catalyst present in the first stage of reaction. Applicants have found, without being bound by or to any particular theory, that the use of such an excess of reactant in the first stage of reaction allows the feed materials to serve as a heat removal medium. Since the reduction or hydrogenation reaction of the present invention is generally exothermic, and usually substantially exothermic, the use of such excess feed material has the effect in preferred embodiments of maintaining the reactor temperature below that which would exist if an excess of feed material were not used, assuming all other process conditions were maintained the same.

Applicants have found that the step of maintaining a very low conversion of reactant in accordance with the present invention in a first stage of reaction has an advantageous affect on the selectivity of the reaction to the desired alkane. In other words, although the amount of conversion which occurs in the first stage of reaction is controlled to be well below that which is desired for the overall reduction step, applicants have found that an improved, higher percentage of the feed material is converted to the desired alkane in the first reaction stage (that is, improved selectivity is achieved) by controlling the conversion as described herein. More specifistep may comprise greater than two reaction stages, including in some embodiments as many 10 or more reaction stages.

In preferred embodiments, the fluorinated olefin conversion step of the present invention comprises about four reaction stages. Although it is understood that the particular parameters used in each reaction stage may vary widely within the scope of the present invention, depending upon many factors, including the desired fluorinated alkane to be produced, the available feedstock, and other specific processing constraints the following Table 1 provides preferred and more preferred ranges of certain process parameters applicable to certain preferred embodiments of the present invention (all numerical values in the table are understood to be preceded by the word "about.")

TABLE 1

|  |  | STAGE 1 | STAGE 2 | STAGE 3 | STAGE 4*** |
|---|---|---|---|---|---|
| REACTION TEMP, C.* | Preferred | 50–100 | 80–120 | 150–200 | 80–120 |
|  | More Preferred | 60–100 | 90–110 | 160–190 | 100–110 |
| CATALYST WEIGHT, %** | Preferred | 1–15 | 5–20 | 15–40 | 40–80 |
|  | More Preferred | 1–5 | 5–15 | 25–35 | 50–70 |
| CONVERSION, WT % | Preferred | 1–85 | 1–85 | 30–99 | 30–99 |
|  | More Preferred | 1–70 | 1–70 | 60–99 | 60–99 |
| SELECTIVITY, WT % | Preferred | 95–99 | 95–99 | 95–99 | 95–99 |
|  | More Preferred | 97–99 | 97–99 | 97–99 | 97–99 |

*As measured by the temperature of the reaction product effluent
**As a weight percentage of total catalyst in all stages
***Optional cally, it is preferred in many embodiments that the selectivity to the desired alkane in the first reaction stage is at least about 80%, more preferably at least about 90%, and even more preferably at least about 95%, and in many preferred embodiments about 97% or greater.

In certain preferred embodiments the step of controlling the conversion in the first reaction stage further includes removing heat from the reaction by cooling at least a portion of the reaction mixture. It is contemplated that those skilled in the art will be able to devise without undue experimentation many means and mechanisms for attaining such cooling in view of the teachings contained herein and all such means and mechanisms are with the scope of the present invention.

Figure 2:
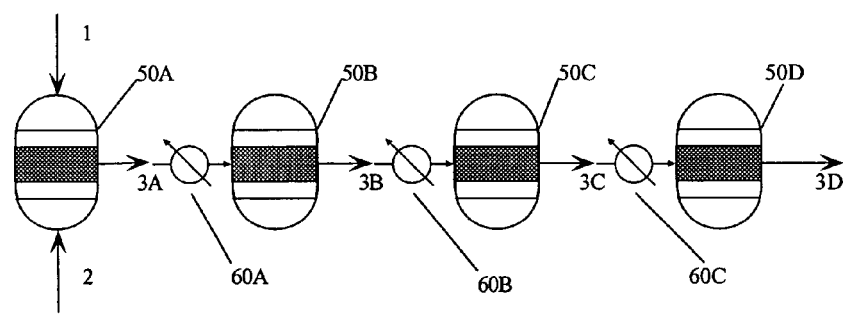
FIG. 2 is a semi-schematic process flow diagram according to one embodiment of the multi-stage hydrogenation step of the present invention.

In preferred embodiments, at least a portion of the effluent from the first reaction stage is fed directly, or optionally after some further processing, to a second reaction stage in which the unreacted fluorinated olefin remaining in the effluent after the first reaction stage is converted to the fluorinated alkane in accordance with the present invention. More specifically it is preferred that the second reaction stage or subsequent reaction stages if present, is/are operated under conditions effective to convert the fluorinated olefin contained in the feed stream to the second reactor stage at a conversion rate that is greater than, and preferably substantially greater than, the conversion percentage in the first reaction stage. In certain preferred embodiments, for example, the conversion percentage in the second reaction stage is from about 20% to about 99%, depending in large part upon the total number of reactant stages used to carry-out the overall conversion step. For example, in embodiments consisting of a two-stage reaction system, it is contemplated that the conversion in the second reaction stage is preferably greater than 95%, and even more preferably about 100%. However, as those skilled in the art will appreciate from the teachings contained herein, such a two-stage reaction may not be sufficient to produce the desired selectivity to the fluorinated alkane. In such cases, it is within the scope of the present invention that the conversion For the purposes of illustration but not necessarily by way of limitation, one arrangement of multiple reaction stages in accordance with a preferred reduction step in accordance with the present invention is illustrated in FIG. 2. Although it is contemplated that the reduction step 50 may be conducted in a batch-wise or semi-continuous operation, it is preferred that the reduction step 50 is a continuous operation of the general type shown in FIG. 2. In FIG. 2, a first stage reactor 50A is provided with catalyst in an amount effective to provide a conversion of the fluorinated olefin contained in stream 1 of from about 10% to about 60% in accordance with the present invention. In preferred embodiments, the first reaction stage of the present invention, for example vessel 50A, is provided with a means for cooling the reaction mixture (not shown). For example, the reaction vessel 50A may be a jacketed reaction vessel in which the space between the vessel and the jacket contains a cooling medium to remove heat from the reactor. Of course, other means for cooling the reaction mixture may be employed, such as the use of an internal cooling coil, the introduction of additional cooling diluent to the reaction mixture, and the like.

The effluent 3A from the first reaction stage is preferably, but not necessarily, further cooled prior to its introduction into the second reaction stage, such as reaction vessel 50B, for example by use of a heat exchanger 60A. In certain embodiments, it may be desirable for the heat exchanger 60A, and/or one or more of the downstream heat exchangers 60B and 60C, to provide the capability of adding heat to the effluent prior to its introduction into the next reaction stage. This capability is desirable in certain embodiments because it is generally, although not exclusively, preferred that the level of conversion in each subsequent reaction stage is higher than in the immediately preceding prior stage. In order to achieve this result, it may be desirable and/or necessary to raise the temperature of one or more of the feed streams as a means for contributing to a higher reaction temperature in the next stage of reaction. Of course, those skilled in the art will appreciate that many means and mechanisms are available for controlling the temperature in all subsequent reaction stages, and all such means and mechanisms are within the scope of the present invention and may be used to control the conversion of the reaction stage in accordance with the present invention.

The size and shape, and other characteristics of the reaction vessel itself may vary widely with the scope of the present invention, and it is contemplated that the vessel associated with each stage may be different than or the same as the vessel associated with the upstream and downstream reaction stages. Furthermore, it is contemplated that all reaction stages can occur inside a single vessel, provided that means and mechanisms necessary to control conversion are provided. For example, it may be desirable in certain embodiments to utilize a single tubular reactor for each reaction stage, providing conversion control by judicious selection of the amount and/or distribution of catalyst throughout the tubular reactor. In such a case, it is possible to further control the conversion in different sections of the same tubular reactor by controlling the amount of heat removed from or added to different sections of the tubular reactor.

Those skilled in the art will be readily able to select the type of catalyst(s) used for the hydrogenation step of the present invention in view of the teachings contained herein. For example, it is preferred in certain embodiments that at least one, but preferably all, reaction stages utilize palladium catalyst, either alone or in combination with other catalysts. In this regard one or more of the hydrogenation catalyst disclosed in U.S. Pat. No. 5,679,875, which is incorporated herein by reference, maybe used for one or more of the reaction stages in accordance with the present invention. In certain preferred embodiments, the catalyst preferably comprises palladium supported on carbon, such as a carbon mesh.

Thus, certain embodiments of the present methods comprise bringing a fluorinated olefin in accordance with formula I and a hydrogenation agent, such as $H_2$, into contact with a first amount of catalyst in a first reaction stage to produce a reaction stream comprising hydrofluorocarbon(s), unreacted fluorinated olefin and hydrogenation agent; contacting at least a portion of this first effluent stream with a second amount of catalyst in a second stage of reaction to produce a hydrofluorocarbon, wherein the second amount of catalyst is greater than the first amount of catalyst and wherein conversion to the fluorinated olefin is higher in the second stage of reaction.

The following examples are given as specific illustrations of the invention. It should be noted, however, that the invention is not limited to the specific details set forth in the examples.

EXAMPLES

Comparative Example C-1

Reaction of Hexafluoropropene and Hydrogen in a Single Stage

A small jacketed, single stage reactor with an outer jacket connected to a circulating cooling bath of 31° C. is charged with 0.2 g of 1% Pd/C (4-6 mesh) mixed with nichrome mesh of a similar size to give a total catalyst bed volume of 1 cc. Prior to the introduction of hydrogen and hexafluoropropene gases, the bed temperature is initially about 21° C. However, when hydrogen (0.37 mol/h) and hexafluoropropene (0.26 mol/h) are introduced, the bed temperature rises to nearly 70° C. in about 1 minute.

Comparative Example C-2

Reaction of Hexafluoropropene and Hydrogen in a Single Stage

The same small, jacketed single stage reactor as in Example C-1 is charged with a small amount of 1% Pd/C. Hydrogen and hexafluoropropene are premixed and then introduced into the reactor. The temperature of the catalyst bed is allowed to stabilize at 69° C. Exit gases are analyzed to determine conversion and selectivity for $CF_3CHFCF_2H$. The average conversion is 93.2% while the average selectivity is 95.7%.

Comparative Example C-3

Reaction of Hexafluoropropene and Hydrogen in a Single Stage

Comparative Example C-2 is repeated using the same single stage reactor, except the temperature of the circulating fluid is reduced to 21° C. The temperature of the bed stabilizes at 61.5° C. Under these conditions, the conversion is reduced to 88.6% while the selectivity increases to 97.0%.

Examples 1 and 2

Multi-Stage Reduction Reactions

The reactors used in the following examples are multi-stage reactors constructed from sections of 1.5" schedule 40, 316 SS pipe.

The amount of catalyst used to charge each reaction stage is calculated by first estimating the productivity of the catalyst (grams of feed converted per gram of catalyst per hour). The productivity is estimated from scoping studies using a small reactor. Next, the desired production rate is set at about 10 pounds per hour, allowing the total amount of catalyst needed for 100% conversion to be estimated. Using this information, an estimated amount of catalyst needed to convert 10-15% of the olefin in the first reactor is calculated.

Catalyst loading in the following examples is as follows:

Section 1 (1.5"×1 foot): 10 g of catalyst (1 wt % Pd on 4-8 mesh carbon) with the remainder filled with ¼" SS protruded packing, catalyst equally distributed throughout.

Section 2 (1.5"×2 foot): 25 g catalyst distributed as in Section 1.

Section 3 (1.5"×3 foot): 73.4 g catalyst with 1200 cc of packing distributed as in Section 1.

Section 4 (1.5"×4 foot): 158 g of catalyst distributed with 1400 cc of packing. Total catalyst=267 g.

Hexafluoropropene is introduced to the multi-stage reactor and reduced continuously over a period of 58 hours during which the average feed rate is 14.5 lb/h (or about 16.4 L per minute). The average hydrogen feed rate is 25 L per minute. Samples are taken at various points along the series of reactors to follow the percent conversion and selectivity. After the second reaction stage, the conversion is about 40%; after the fourth reaction stage, the conversion is 99.5% with selectivity for $CF_3CHFCF_2H$ of 99%. The temperature of the gases immediately exiting the reaction stages is 66° C. for the first stage, 104° C. for the second stage, 173° C. for the third stage, and 100° C. for the fourth stage. The maximum temperature in any reaction stage is about 230° C. The first bath is maintained at 55° C. while the second bath is maintained at 111° C.

Example 2

Multi-stage Reduction of 1,2,3,3,3-Pentafluoropropene-1

1,2,3,3,3-Pentafluoropropene-1 is hydrogenated using the same reactor as in Example 1 using a feed rate of 14.6 lb/h for a total of 64 hours. The average hydrogen feed rate is 25 liters per minute. Samples are taken at various points along the series of reactors to follow the percent conversion and selectivity. After the second reactor, the conversion is about 54%. While after the fourth reactor, the conversion is 100% with the selectivity for $CF_3CHFCH_2F$ of 98%. The temperature of the gases immediately exiting the reactors is 99° C. for the first reactor, 95° C. for the second reactor, 173° C. for the third reactor, and 104° C. for the fourth reactor. The maximum temperature in any reactor is about 240° C. The first bath is maintained at 59° C., and the second bath is maintained at 116° C.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the spirit and script of the invention, and all such variations are intended to be included within the scope of the following claims.

What is claimed is:

1. A process for the production of a fluorinated propane comprising the steps of:
   (a) contacting, in a first reaction stage, a feed stream comprising a fluorinated olefin and a reducing agent with a first amount of catalyst to produce at least a first effluent stream comprising a flurorinated alkane, unreacted fluorinated olefin, and reducing agent,
      wherein said fluorinated olefin is fed into said first reaction stage at a rate that is at least about 60% above the productivity of the catalyst present in said first reaction stage and results in a conversion of the fluorinated olefin to a fluorinated alkane of from about 10% to about 60%;
   (b) contacting, in one or more additional reaction stages, said first effluent stream with a second amount of catalyst to produce said fluorinated alkane, said second amount of catalyst being present in an amount to achieve a conversion to said fluorinated olefin substantially greater than in the conversion of said fluorinated olefin in said first reaction stage,
   wherein said fluorinated olefin is a compound of formula (I):

$$(CX_nY_{3-n})(CR^1_aR^2_b)_ZCX{=}CH_mX_{2-m} \qquad (I)$$

and said fluorinated alkane is a compound of formula (II):

$$(CX_nY_{3-n})(CR^1_aR^2_b)_ZCHXCH_2X \qquad (II)$$

where:
   each X is independently Cl, F, I or Br;
   each Y is independently H, Cl, F, I or Br;
   each R1 is independently H, Cl, F, I, Br or unsubstituted or halogen substituted methyl or ethyl radical;
   each $R^2$ is independently H, Cl, F, I, Br or unsubstituted or halogen substituted methyl or ethyl radical;
   n is 1, 2 or 3;
   a and b are each 1 or 2, provided that a+b=2;
   m is 0, 1 or 2; and
   Z is 0, 1, 2 or 3.

2. The process of claim 1 wherein said fluorinated olefin comprises hexafluoropropene.

3. The process of claim 1 wherein said fluorinated olefin comprises pentafluoropropene.

4. The process of claim 1 wherein said fluorinated alkane comprises chlorotrifluoropropane (HCFC-244).

5. The process of claim 1 wherein said fluorinated alkane comprises pentafluorpropane (HFC-245).

6. The process of claim 1 wherein said fluorinated alkane comprises hexafluoropropane (HFC-236).

7. The process of claim 1 wherein said fluorinated alkane comprises 1,1,1,2,3-pentafluoropropane (HFC-245eb).

8. The process of claim 1 wherein said reducing agent comprises hydrogen and each of said contacting steps comprises a catalytic hydrogenation reaction.

9. The process of claim 8 wherein each of said contacting steps comprises the use of carbon-supported palladium.

10. The process of claim 1 wherein said fluorinated olefin is fed into said first reaction stage at a rate that is at least about 90% above the productivity of the catalyst present in said first reaction stage.

11. The process of claim 1 wherein said conversion of said fluorinated olefin in said second reaction stage is from about 20% to about 99%.

12. The process of claim 1 wherein said conversion of said fluorinated olefin in said second reaction stage is greater than about 95%.

13. The process of claim 1 wherein said contacting step (b) occurs in one additional reaction stage.

14. The process of claim 1 wherein said contacting step (b) occurs in three additional reaction stages.

15. A process for the production of a fluorinated propane comprising the steps of:
   a. selecting a first amount of a predetermined catalyst theoretically needed to reduce a fluorinated olefin at a conversion rate of about 10 to about 60 percent;
   b. contacting, in a first reaction stage, a feed stream comprising a fluorinated olefin and a reducing agent with a first amount of catalyst to produce at least a first effluent stream comprising a flurorinated alkane, unreacted fluorinated olefin, and reducing agent wherein a conversion of the fluorinated olefin to a fluorinated alkane is from about 10% to about 60%;
   c. contacting, in one or more additional reaction stages, said first effluent stream with a second amount of catalyst to produce said fluorinated alkane, said second amount of catalyst being present in an amount to achieve a conversion to said fluorinated olefin substantially greater than in the conversion of said fluorinated olefin in said first reaction stage,
   wherein said fluorinated olefin is a compound of formula (I):

$$(CX_nY_{3-n})(CR^1_aR^2_b)_ZCX{=}CH_mX_{2-m} \qquad (I)$$

and said fluorinated alkane is a compound of formula (II):

$$(CX_nY_{3-n})(CR^1_aR^2_b)_ZCHXCH_2X \qquad (II)$$

where:
   each X is independently Cl, F, I or Br;
   each Y is independently H, Cl, F, I or Br;
   each R1 is independently H, Cl, F, I, Br or unsubstituted or halogen substituted methyl or ethyl radical;
   each $R^2$ is independently H, Cl, F, I, Br or unsubstituted or halogen substituted methyl or ethyl radical;
   n is 1, 2 or 3;
   a and b are each 1 or 2, provided that a+b=2;
   m is 0, 1 or 2; and
   Z is 0, 1, 2 or 3.

* * * * *